United States Patent
St. George

(10) Patent No.: US 9,895,157 B2
(45) Date of Patent: Feb. 20, 2018

(54) MECHANICAL CONVERTER ASSEMBLY AND IMPLEMENTATIONS

(71) Applicant: Gyrus ACMI, Inc., Southborough, MA (US)

(72) Inventor: Lawrence J. St. George, Sudbury, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 14/687,166

(22) Filed: Apr. 15, 2015

(65) Prior Publication Data

US 2015/0327877 A1    Nov. 19, 2015

Related U.S. Application Data

(60) Provisional application No. 61/992,259, filed on May 13, 2014.

(51) Int. Cl.
  *A61H 1/00* (2006.01)
  *A61B 17/22* (2006.01)
  *F16H 25/18* (2006.01)

(52) U.S. Cl.
  CPC .. *A61B 17/22004* (2013.01); *A61B 17/22012* (2013.01); *F16H 25/183* (2013.01); *A61B 2017/22015* (2013.01)

(58) Field of Classification Search
  CPC .............................. A61B 17/2251; G10K 15/06
  See application file for complete search history.

(56) References Cited

U.S. PATENT DOCUMENTS

| | | | |
|---|---|---|---|
| 2,693,708 A | 11/1954 | Baer, Sr. et al. |
| 4,765,690 A | 8/1988 | Rudiger et al. |
| 5,090,262 A | 2/1992 | Klein |
| 5,111,659 A | 5/1992 | Klein |
| 5,449,363 A | 9/1995 | Brust et al. |
| 5,951,570 A | 9/1999 | Leibersperger et al. |
| 6,261,298 B1 | 7/2001 | Irion et al. |

(Continued)

FOREIGN PATENT DOCUMENTS

| | | |
|---|---|---|
| JP | H11-257452 | 9/1999 |
| JP | 2002-336265 | 11/2002 |

OTHER PUBLICATIONS

International Search Report, PCT/US2015/025898, dated Jul. 15, 2015, pp. 4.

*Primary Examiner* — Hien Nguyen
(74) *Attorney, Agent, or Firm* — Gerald P. Kazanjian; Pegah Karimi

(57) ABSTRACT

A mechanical converter assembly includes an input, a lever stack (multiple levers), and an output. The input is configured to receive a mechanical drive force (or mechanical input signal) from a driver resource. The lever stack translates the received drive force into a mechanical output force (or mechanical output signal). The output of the mechanical converter assembly is configured to apply the mechanical output force produced by the lever stack to a driven element. In one embodiment, use of the lever stack in the mechanical converter assembly provides translational gain in which an amount of translational movement at the input of the mechanical converter assembly results in a substantially greater amount of corresponding translational movement at the output.

11 Claims, 11 Drawing Sheets

(56) References Cited

U.S. PATENT DOCUMENTS

| | | | |
|---|---|---|---|
| 7,290,841 B2* | 11/2007 | Isono | B60T 8/367 |
| | | | 303/11 |
| 8,579,808 B2 | 11/2013 | Schulte | |
| 2002/0117049 A1* | 8/2002 | Wang | F01B 11/02 |
| | | | 91/422 |
| 2008/0009884 A1 | 1/2008 | Kennedy, II | |
| 2010/0228268 A1* | 9/2010 | Hiranuma | A61B 17/076 |
| | | | 606/138 |
| 2011/0288457 A1 | 11/2011 | Questo et al. | |
| 2012/0209174 A1 | 8/2012 | Moll et al. | |
| 2014/0046339 A1 | 2/2014 | Bonuttti | |

* cited by examiner

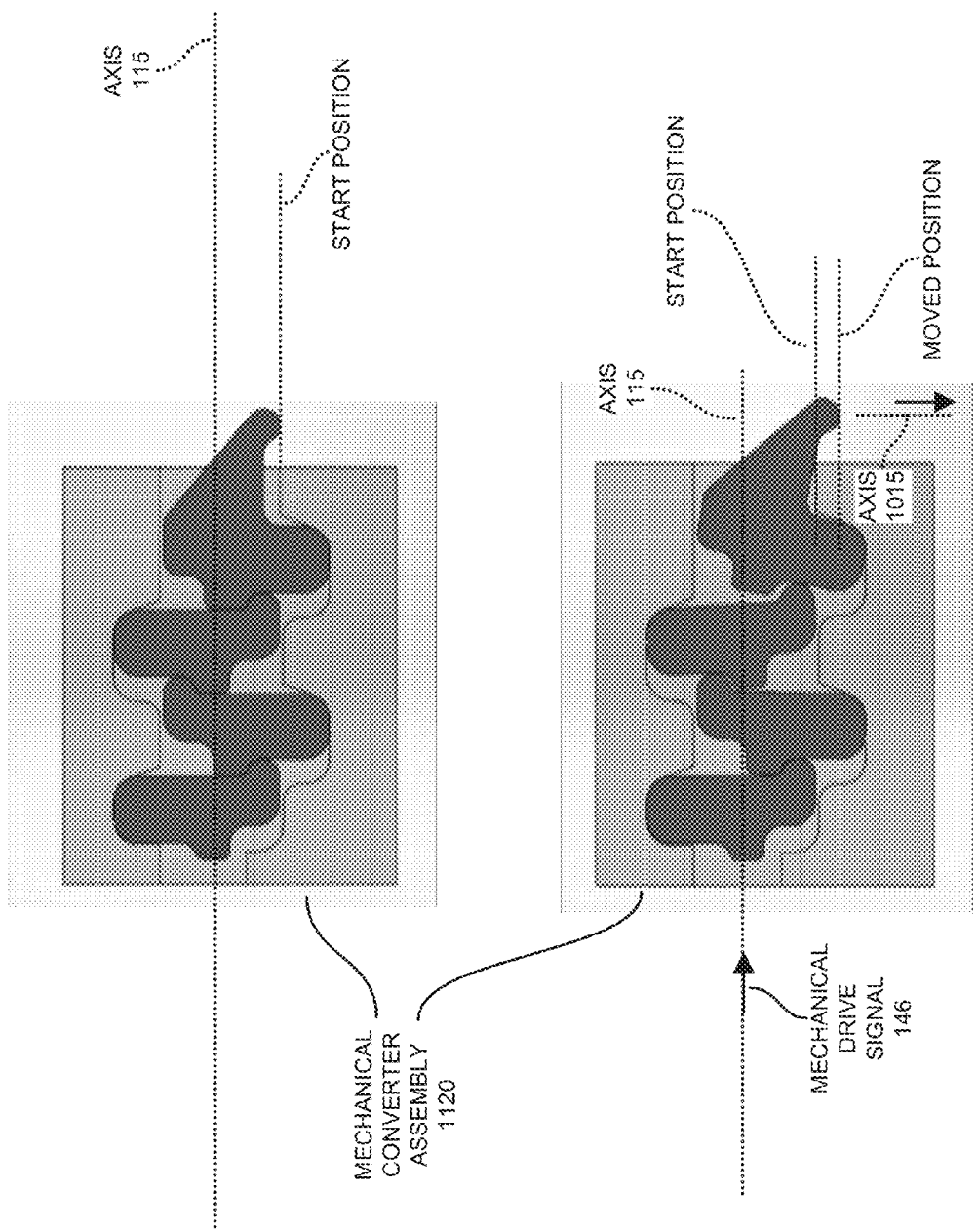

MECHANICAL CONVERTER ASSEMBLY AND IMPLEMENTATIONS

RELATED APPLICATIONS

This application is related to and claims the benefit of earlier filed U.S. Provisional Patent Application Ser. No. 61/992,259 entitled "MECHANICAL CONVERTER ASSEMBLY AND IMPLEMENTATIONS,", filed on May 13, 2014, the entire teachings of which are incorporated herein by this reference.

BACKGROUND

Ultrasonic and pneumatic lithotripsy or so-called stone-breaking devices have been available for medical use for a number of decades. Currently, there exist a number of rigid solid tubular shaft-based lithotripsy devices that use ultrasonic or pneumatic energy to break a respective stone down into smaller pieces for easier removal from a respective patient's urologic system.

In general, during use of a shaft-based lithotripsy device, ultrasonic acoustic frequency energy is transmitted (translated) down a stiff metal shaft and delivered by contact to a kidney stone. The tips of tubes or shafts in such devices are typically terminated with a flat surface. For procedures performed with the tubular shaft device, liquid and debris can be sucked through the center of the tubular shaft.

Some devices incorporate and deliver a lower frequency energy component to the kidney stone either through the same shaft or via a second shaft; the second shaft is usually coaxial to an ultrasonic energy shaft. Presence of the additional secondary, lower frequency shaft shows evidence of improving the stone breaking efficiency in comparison to an approach in which only a single ultrasonic energy and corresponding shaft is used to break up a kidney stone.

Typically, the use of such a lithotripsy device requires that the stone being broken is pressed up against some surface, usually an inner wall of the kidney, in order that the vibrational energy from the tip of the tool can be sufficiently delivered to the stone surface to break it up. Some devices in the market offer a combination of a lithotripsy shaft and a stone basket where the lithotripsy shaft is incorporated into the center of the lithotripsy basket; the shaft and emerges into the center of the lithotripsy basket. This design offers the ability to apply the pneumatically driven shaft to a kidney stone contained in the associated basket, or if the kidney stone is too large, to extend the shaft beyond the basket to break up a stone into smaller components which then can be captured within the associated basket.

The size, stiffness, and length of the straight shafts in much of the existing ultrasonic lithotripter technology only allow the use of such devices with large shafts in percutaneous procedures (i.e., direct access to stones in the kidney through a small incision in the patient's back and through the kidney itself). Percutaneous procedures are usually only performed in the United States for very large kidney stones, in lieu of addressing such stones via flexible scope procedures, which would require a very long duration to complete. Percutaneous procedures seem to be more frequently used in countries outside of the United States, possibly due to the high cost and usually fragile nature of the flexible ureteral scopes. There is some evidence that percutaneous procedures are even used for smaller stones outside of the United States, possibly due to cost and fragility of, and risk to flexible ureteroscopes.

Laser lithotripsy is a strong competitor of ultrasonic lithotripsy. Laser energy passing through the laser fibers can be used to very effectively break the kidney stones in virtually any area of the urinary system. When used with flexible ureteroscopes, laser fibers can bend around corners and access kidney stones in the lower pole of the kidney. Perhaps since lasers have been known to break in the working channel and damage flexible ureteroscopes, techniques have been developed to access and retrieve kidney stones in the lower pole of the kidney and move them to a different location such as the upper pole of the kidney where they are more accessible.

Electrohydraulic lithotripsy (EHL) has similar ease and access via flexible endoscope to laser lithotripsy with generally lower cost, but with also generally lower stone fragmentation efficiency. When using this technology, there are also some concerns about local shockwave effects of nearby tissue.

Most, if not all, current ultrasonically or pneumatically driven lithotripsy shafts are distally terminated to be smooth and perpendicular to the shaft axis. This smooth, flat surface, while providing more protection to soft tissue because of its smoothness, can make it extremely easy for the activated shaft to slip off the stone, or for the stone to slide out from beneath the vibrating smooth tip. This may prolong duration of a stone breaking procedure because the physician must "chase" the stone around to break it up.

A common design configuration for an ultrasonic lithotripsy drive component tends to be a stack assembly of piezoelectric discs, such as 4 to 6 in number, with an approximately 15 to 20 millimeter outside diameter, a length of approximately 20 to 30 millimeters, and an inner diameter of approximately 7 to 10 millimeters. Each piezoelectric disk in such a stack assembly can have a thickness of about 3 to 4 millimeters. The stack configuration provides for multiplication of the dimensional changes each piezoelectric disk undergoes with various voltage levels and polarities are applied across the body of each disk.

The thickness of each disk is part of what determines the voltage that must be applied to achieve a specific dimensional change. For example, if one disk expands longitudinally by 1 μm (micrometer) from application of certain voltage potential at the two main faces of the respective disk, a stack of 6 such disks, with each disk subjected to the same voltage potential applied across it should expand by 6 μm. The longitudinal expansion of the disk can be further increased by the utilization of a focusing cone configuration, which then transfers and magnifies the disks longitudinal expansion to drive a lithotripsy shaft forward and backwards and/or excite longitudinal vibration energy in the shaft.

Such configurations, especially with individual piezoelectric disks with a thickness of 3-4 millimeters, require either significantly high voltages to induce significant dimensional changes, or are highly dependent on operating at a specific resonant frequency to be effective when using drive voltages within a practical range. Other components coupled to such drivers must conform to particular resonant frequency requirement in order to be effective with such a drive that has a resonance dependence for effective operation.

Thinner piezoelectric discs are much more responsive to voltage stimulus than are thicker discs. Stack assemblies with thinner piezoelectric disks are less dependent on a specific resonant frequency to be effective at a longitudinal dimension change, but to achieve the same level of overall longitudinal dimension change, many more elements are needed (to essentially achieve the same total thickness of a thick disk stack). Thus, complexity and price of a respective driver rise considerably when using thinner disks.

BRIEF DESCRIPTION

Conventional techniques of providing translational motion in a tool suffer from deficiencies. For example, as previously discussed, translational movement of a shaft can be achieved via an excitation of multiple disks in a piezoelectric stack. However, the amount of translational movement provided by the piezoelectric stack may be limited. Certain applications may require a longer reciprocating stroke to perform a task such as pulverize a kidney stone. Thus, the ability to perform useful operations with a conventional hand tool may be limiting because of the inability to provide a proper stroke length.

One embodiment herein includes providing a novel and useful way of providing translational gain. For example, one embodiment herein includes a mechanical converter assembly. The mechanical converter assembly can be disposed in any suitable device such as a hand tool. In one embodiment, the mechanical converter assembly includes an input, a lever stack, and an output. The input can be configured to receive a drive force (or mechanical input signal) from a driver resource. The lever stack includes one or more levers that translate the received drive force into a mechanical output force (or mechanical output signal). The output of the mechanical converter assembly is configured to apply the mechanical output force produced by the lever stack to a driven element such as shaft.

In one embodiment, as mentioned, use of the lever stack in the mechanical converter assembly provides translational gain in which an amount of translational movement at the input of the mechanical converter assembly results in a substantially greater amount of corresponding translational movement at the output of the mechanical converter assembly.

As a more specific example, assume that the driver resource produces a reciprocating mechanical drive force (such as a back-and-forth motion) inputted into an input element of the mechanical converter assembly. The mechanical converter assembly, and corresponding lever stack of multiple levers, magnifies the received back-and-forth motion to produce a back-and-forth output motion at the output of the mechanical converter assembly. In one embodiment, the stroke length of the back-and-forth motion outputted from the output of the mechanical converter assembly is substantially greater than the stroke length of the received back-and-forth motion at the input of the mechanical converter assembly.

In accordance with further embodiments, the mechanical converter assembly (and corresponding lever stack) increases a respective stroke length of a received mechanical signal at the expense of the amount of force provided at the output. For example, in one embodiment, a magnitude of the mechanical output force produced and outputted by the lever stack of the mechanical converter assembly is substantially less than a magnitude of the mechanical drive force received at the input.

The mechanical converter assembly as described herein can be used in any suitable application. One embodiment herein includes use of the mechanical converter assembly in a hand tool such as a lithotripsy medical device. The lithotripsy medical device can be configured to include a driver resource, the mechanical converter assembly, and a driven element (such as a shaft). The driver resource produces a mechanical drive force inputted to the mechanical converter assembly. As previously discussed, based on the received mechanical drive force, the mechanical converter assembly (and corresponding multiple levers) produces a mechanical output force that translationally moves the driven element. In one embodiment, the gain in translation movement as provided by the multiple levers in the mechanical converter assembly causes a back-and-forth stroke of the drive element (such as a shaft) to be substantially greater than if the drive element was driven directly by the driver resource. Thus, the mechanical converter assembly as described herein provides increased motion over conventional techniques.

Embodiments herein are beneficial over conventional techniques. For example, conventional movement of a shaft is limited based on an ability of a driver resource to produce a sufficiently long input stroke. In contrast to conventional techniques, embodiments herein include inclusion of a mechanical converter assembly to provide a longer stroke as opposed to burdening the driver resource to provide a longer stroke.

Further embodiments herein provide the ability to utilize a mechanical converter assembly that is less dependent on resonance for effective operation than the prior art. The mechanical converter assembly can convert motion (energy) received from a driver resource such as a piezoelectric disk stack and convert it to advantageous forms depending on a respective one or multiple shaft designs. Still further embodiments herein provide for a modular approach to assembling a lithotripsy shaft system, giving more flexibility to adapt the applied lithotripsy energy to the existing conditions at the time of use, or to beneficially augment the operation or different shaft configurations while utilizing a standard driver configuration. Hence, shafts or applications of a shaft, which may benefit more from shorter strokes and stronger impulses would be best coupled directly to an impulse driver such as a piezoelectric stack via a mechanical converter assembly providing only a relatively small amount of movement magnification. Alternatively, shafts or applications of shafts, which may benefit from longer strokes but do not require stronger impulses, can be coupled to an impulse driver via a mechanical converter assembly, which provides a comparatively higher amount of movement magnification. Thus, depending on the application, one can choose a mechanical converter assembly having a high or low amount of translational gain for use in a particular type of hand tool and corresponding shaft.

In accordance with further embodiments, the multiple levers are fabricated from elastic material. Translation of a received mechanical drive force through the lever stack at least partially deforms the multiple levers from their respective original shapes such that the lever stack compresses at least by some amount. Subsequent to dissipation of the received mechanical drive force, the multiple levers revert back to their respective original shapes.

In accordance with yet further embodiments, the lever stack of multiple levers between the input and the output compresses during translation of the received drive force due to flexing of one or more of the multiple levers in the lever stack. The multiple levers revert back to their original shapes upon dissipation of the translated force. Thus, the lever stack, itself, disposed between a respective input and output can be configured to have compressible spring-like qualities.

These and other embodiment variations are discussed in more detail below.

Note that embodiments herein can include a configuration of one or more computerized devices, hardware processor devices, assemblers, fabricator resources, or the like to carry out and/or support any or all of the method operations disclosed herein. In other words, one or more computerized devices, processors, digital signal processors, assemblers, etc., can be programmed and/or configured to perform the method as discussed herein.

Additionally, although each of the different features, techniques, configurations, etc., herein may be discussed in different places of this disclosure, it is intended that each of the concepts can be executed independently of each other or in combination with each other. Accordingly, the one or more present inventions, embodiments, etc., as described herein can be embodied and viewed in many different ways.

Also, note that this preliminary discussion of embodiments herein does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

FIG. 11 is an example side-view diagram illustrating a mechanical converter assembly according to embodiments herein.

Figure 1:
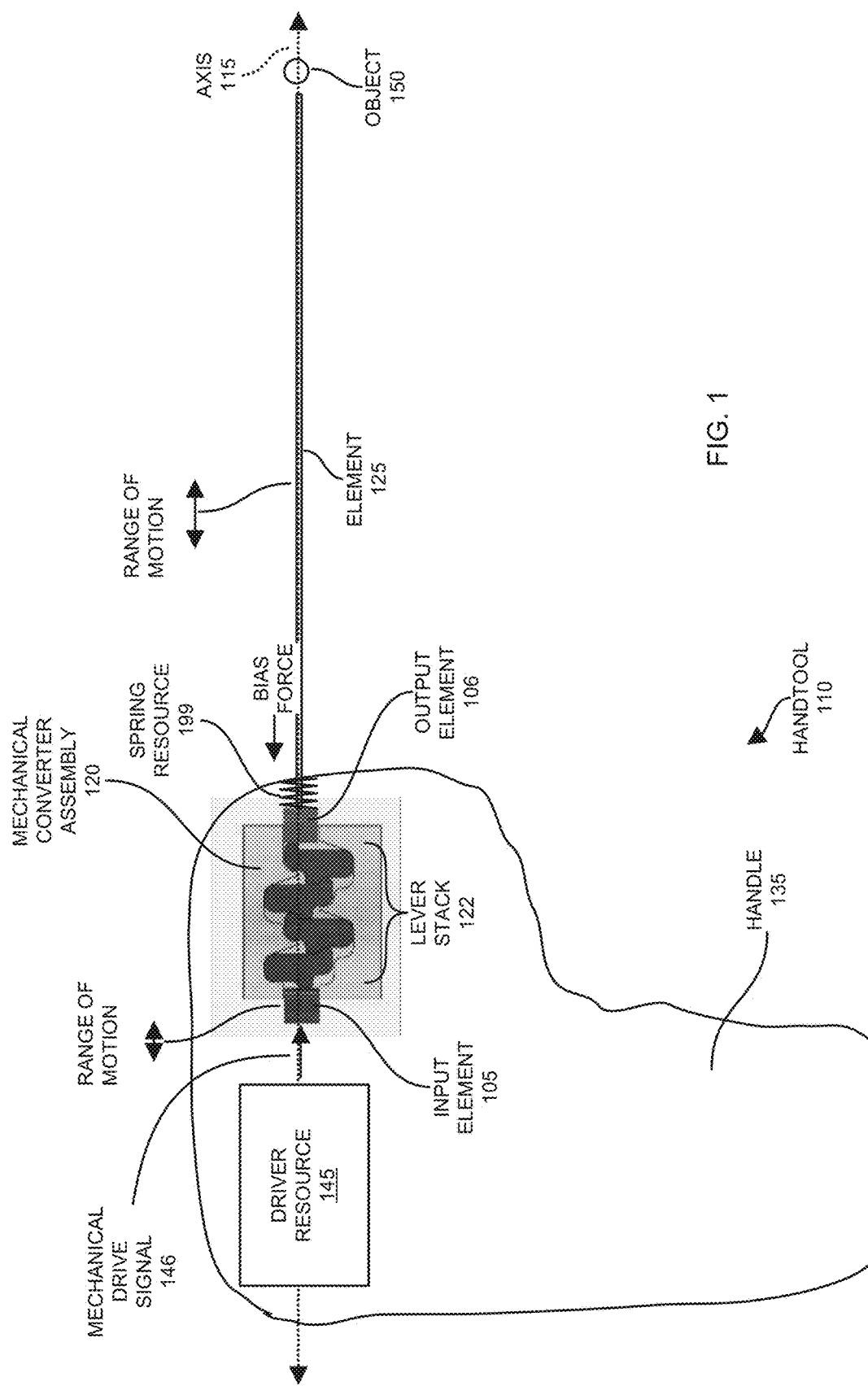
FIG. 1 is an example side-view diagram of a mechanical converter assembly disposed in a hand tool according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

Now, more specifically, FIG. 1 is an example diagram of a hand tool including a mechanical converter assembly according to embodiments herein.

As shown, hand tool 110 includes handle 135, driver resource 145, mechanical converter assembly 120, and element 125.

In general, during operation, driver resource 145 produces mechanical drive signal 146. Input element 105 at the input of mechanical converter assembly 120 receives mechanical drive signal 146. Via lever stack 122 (including multiple levers), the mechanical converter assembly 120 converts received mechanical drive signal 146 (such as a mechanical drive force) into a respective mechanical output signal (or output drive force) that is outputted from the mechanical converter assembly 120 at the output element 106.

In one embodiment, the driver resource 145 produces a translational motion that is inputted to input element 125 of mechanical converter assembly 120. Mechanical converter assembly 120 converts the received translational motion into a magnified output translational motion applied to element 125. The back-and-forth (or reciprocating) motion of element 125 along axis 115 can be directed to pulverize object 150.

Figure 2:
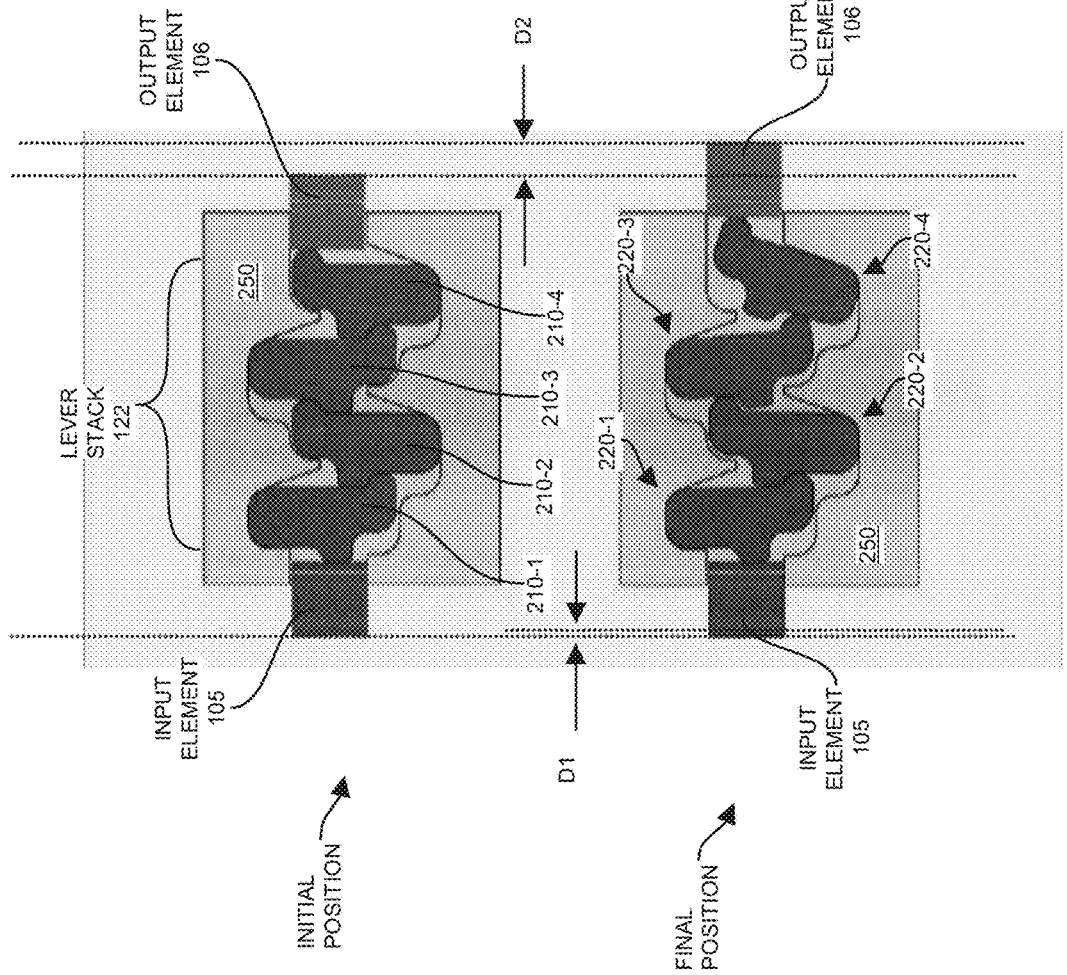
FIGS. 2A and 2B are example side-view diagrams illustrating details of a mechanical converter assembly in multiple different states according to embodiments herein.

FIG. 2A is an example diagram more particularly illustrating functionality associated with mechanical converter assembly in an initial state according to embodiments herein. As shown in an initial state in FIG. 2A, lever stack 122 includes lever 210-1, lever 210-2, lever 210-3, and lever 210-4 disposed in housing 250.

FIG. 2B illustrates the mechanical converter assembly 120 after the mechanical drive signal 146 is applied to input element 105, causing corresponding translational motion along levers 210 (lever 210-1, lever 210-2, lever 210-3, lever 210-4).

More specifically, mechanical converter assembly 120 includes housing 250 and respective cavities in which the multiple levers 210 and additional corresponding components such as input element 105 as well as output element 106 reside. The housing 250 and one or more of respective components (such as levers 210, input element 105, output element 106) can be fabricated from any suitable material such as metal, hard plastic, etc. In one non-limiting example embodiment, a core of the levers 210, input element 105, and output element 106 are made from steel. Exposed surfaces of the levers 210, input element 105, output element 106, etc., are coated with a slippery or low frictionless material such as Teflon (such as Polytetrafluoroethylene) to facilitate free movement of the components within housing 250.

During operation, by way of non-limiting example, each of the levers pivots about a respective surface in the housing 250. For example, as shown in FIG. 2B, when a sufficient force is applied to input element 105, the lever 210-1 pivots with respect to inner surface 220-1 of housing 250; the lever 210-2 pivots with respect to inner surface 220-2 of housing 250; the lever 210-3 pivots with respect to inner surface 220-3 of housing 250; the lever 210-4 pivots with respect to inner surface 220-4 of housing 250.

Note that inclusion of four levers 220 in mechanical converter assembly 120 is shown by way of non-limiting example only. Note that the mechanical converter assembly 120 can include any suitable number of levers.

As further shown, the input element 105 translates the force (and motion) of received mechanical drive signal 146 at input element 105 to the lever 210-1. As previously mentioned, lever 210-1 pivots with respect to surface 220-1, translating a respective force (and motion) originating from mechanical drive signal 146 (as received through input element 105) to lever 210-2. Lever 210-2 pivots with respect to surface 220-2, translating a respective force (and motion) received from lever 210-1 to lever 210-3. Lever 210-3 pivots with respect to surface 220-3, translating a respective force (and motion) from lever 210-2 to lever 210-4. Lever 210-4 pivots with respect to surface 220-4, translating a respective force (and motion) from lever 210-3 to the output element 106 of mechanical converter assembly 120.

As shown, application of the force associated with mechanical drive signal 146 to input element 105 causes a translational movement of input element 105 and output element 106 along axis 115. During operation, each of the levers 210 in the lever stack of mechanical converter assembly 120 translates a received force and motion up the stack from the input element 105 to the output element 106.

In one embodiment, a magnitude of force associated with the received mechanical drive signal 146 varies over time. By way of non-limiting example, the variations in the magnitude of the mechanical drive signal 146 causes the driven element 125 to reciprocate along a respective translational axis 115. In other words, the mechanical movement of the input element 105 causes movement of the output element 106. Movement of the output element 106 of mechanical converter assembly 120 causes translational movement (switching between initial and final positions shown in FIG. 2A and FIG. 2B) of element 125 (such as shaft) along axis 115.

Referring again to FIG. 1, the mechanical converter assembly 120 can be configured to include a respective spring resource 199 or other suitable resource to apply a bias force to the multiple levers in a direction substantially opposite the received mechanical drive signal 146 (force). In one embodiment, the outputted mechanical force at output element 106 can easily overcome a bias force applied by the spring resource 199. This ensures that the components such as input element 105, levers 210, and output element 106 of the mechanical converter assembly 120 in FIG. 2B all return back to their original states as shown in FIG. 2A when substantially little or no force is applied to the input element 105.

In accordance with further embodiments, note that spring action can be integrated into levers 210 of lever stack 122. For example, one embodiment herein includes adding spring action to the lever stack 122 via forming the levers 210 from any suitable type of flexible material (such as plastic, rubber, metal, etc.) that has inherent elasticity. The flexible material can be one in which the levers 210 change form such as bend, arch, curve, deform, etc., when a force is applied to input element 105 and translates through the lever stack 122 to the output element 106. Subsequent to removal or dissipation of the translated force through the lever stack 122, the levers 210 retain (revert back to) their original shapes again.

Additionally or alternatively, note that embodiments herein can include modifying a shape of the levers 210 to take enhance or provide elasticity. For example, in one embodiment, thinning of one or more levers 210 in the lever stack 122 in certain areas such as along a respective axial length of the lever allows and promotes a bending or flexing action in such thinned regions.

If desired, fabrication of the levers 210 using elastic, flexible material can be combined with the shape thinning to form, for example, an integrated leaf-spring.

In accordance with further embodiments, adding the spring action in the lever stack 122 (such as via forming the levers 210 from flexible material and/or thinning the levers 210), allows the lever stack 122 to resonate in a desired fashion and thereby enhance overall performance. In certain instances, fabrication of the lever stack 122 to have spring-like qualities and resonating properties, reduces the need to include spring resource 199 in the hand tool 110. In other words, in one embodiment, the spring resource 199 may be omitted from hand tool 110 (such that the element 125 directly contacts the output element 106) when the levers 210 in the lever stack 122 are thinned and/or made of suitably flexible material that reverts back into an original shape after a respective translated force dissipates.

In accordance with further embodiments, even though the levers are formed of flexible material or thinned, the spring resource 199 can be included in the hand tool 110 since the spring interaction of spring resource 199 with the lever stack 122 may be lost with the removal of the spring resource 199, such as a force reference connection with the body of the housing that assists in returning the lever stack 122 to an initial positional configuration. As shown and as previously discussed in FIGS. 2A and 2B, the movement of the input element 105 as caused by the mechanical drive signal 146 is magnified by the levers 210 in mechanical converter assembly 120. In this example embodiment, mechanical drive signal 146 causes the input element 105 to move by a distance, D1. The levers 210 cause the output element 106 to move by a distance, D2. By way of non-limiting example, assuming that the distance, D1, is 1 μm and the distance, D2, is 60 μm, the overall translational (or motion) gain from the input of the mechanical converter assembly 122 the output of the mechanical converter assembly 120 is (60/1) sixty.

Of course, the amount of translational gain provided by the mechanical converter assembly 120 can depend on a number of levers disposed in lever stack 122, dimensions of levers, etc. The design parameters (such as dimensions of each lever, number of levers, etc.) of the mechanical converter assembly 120 can be modified to provide any suitable amount of translational gain.

In the above example, for each full stroke, corresponding element 125 moves back-and-forth 60 μm instead of moving back-and-forth only one micrometer if the element 125 was directly coupled to the drive resource 145. In other words, without the gain provided by mechanical converter assembly 120, the driver resource would only be able to move the element 125 back-and-forth by 1 μm. Thus, presence of the mechanical converter assembly 120 is useful to provide an increased amount of reciprocating translational motion along axis 115.

In one embodiment, because of the gain, the translational gain provided by mechanical converter assembly 120 results in a condition in which a magnitude of the mechanical output force produced at the output element 105 of the lever stack is substantially less than a magnitude of force associated with the received mechanical drive signal 146.

Figure 10:
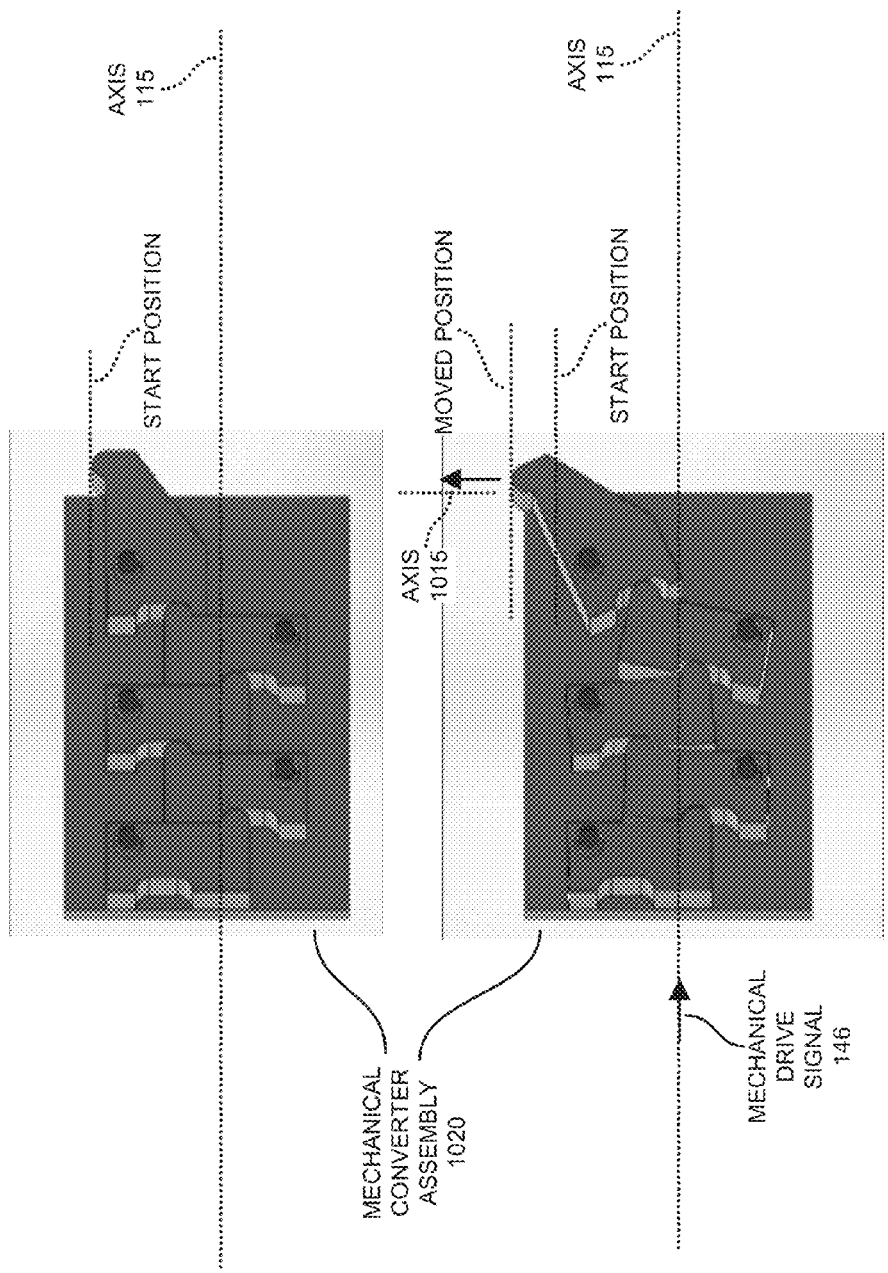
FIG. 10 is an example perspective-view diagram illustrating a mechanical converter assembly according to embodiments herein.

In another embodiment, the direction of mechanical stroke can be changed by the shape of a lever and the location of the pivot point in relation to the contact points on the lever as in FIG. 10 as well as in FIG. 11.

Referring again to FIG. 1, note that element 125 can be made from any suitable one or more rigid or semi-rigid material such as metal (steel, copper, metal alloy, plastic, etc.). By way of non-limiting example, the element 125 can be made from stainless steel.

In one embodiment, the hand tool 110 is used in lithotripsy. As previously discussed, element 125 can be a rigid or semi-rigid shaft. Object 150 can be a kidney stone that is to be pulverized by the reciprocating (or translational) movement of element 125 along axis 115. As previously discussed, the increased translational movement of the element 125 (as afforded by mechanical converter assembly 120) is able to more quickly perform a respective task such as pulverize object 150 into smaller parts.

Figure 3:
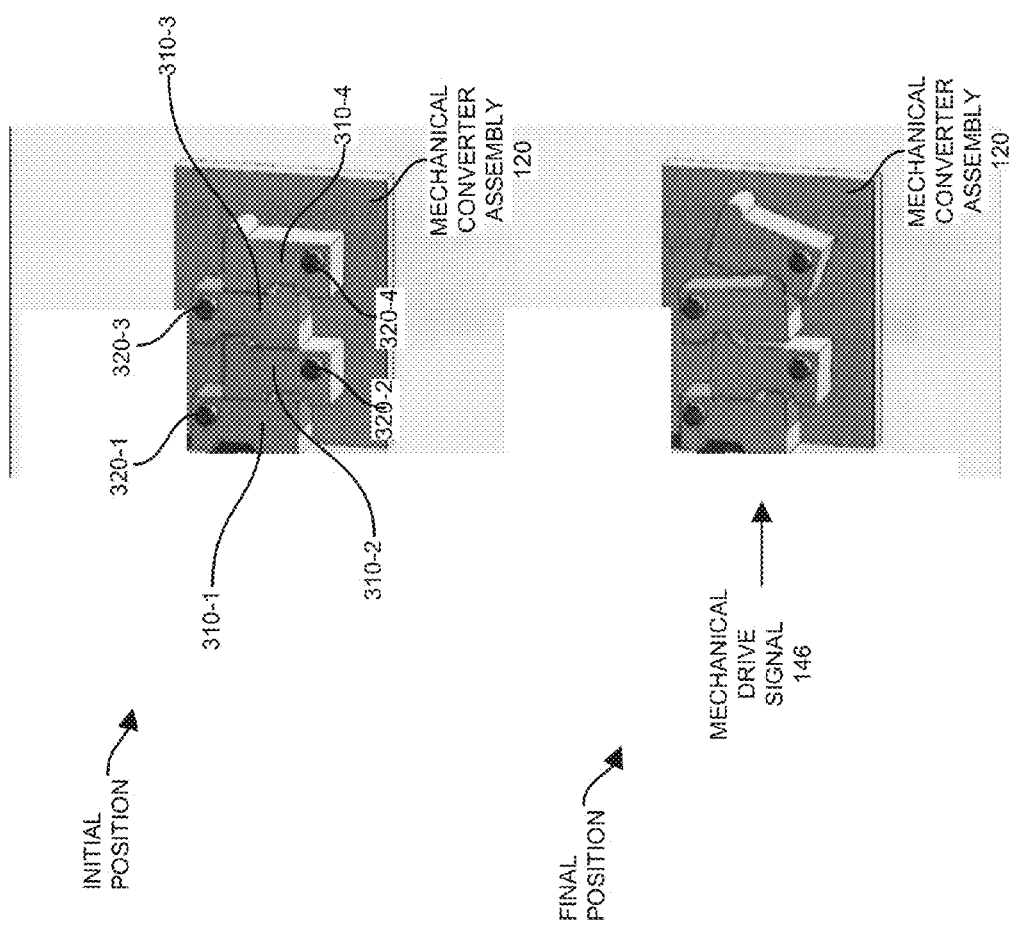
FIG. 3 is an example side-view diagram illustrating details of a mechanical converter assembly in multiple different states according to embodiments herein.

FIG. 3 is an example diagram illustrating details of a mechanical converter assembly according to embodiments herein.

In this example embodiment, the mechanical converter assembly 120 operates in a similar manner as previously discussed. However, mechanical converter assembly 120 includes multiple pins 320 (such as pin 320-1, pin 320-2, and 320-3, and pin 320-4), instead of respective surfaces 220 (surface 220-1, surface 220-2, surface 220-3, and surface 220-4 as discussed in FIGS. 2A and 2B), about which each respective lever pivots. For example, lever 310-1 pivots about pin 320-1; lever 310-2 pivots about pin 320-2; lever 310-3 pivots about pin 320-3; lever 310-4 pivots about pin 320-4.

Thus, any suitable pivoting techniques can be used to provide lever operation and respective gain in the mechanical converter assembly 120.

Figure 4:
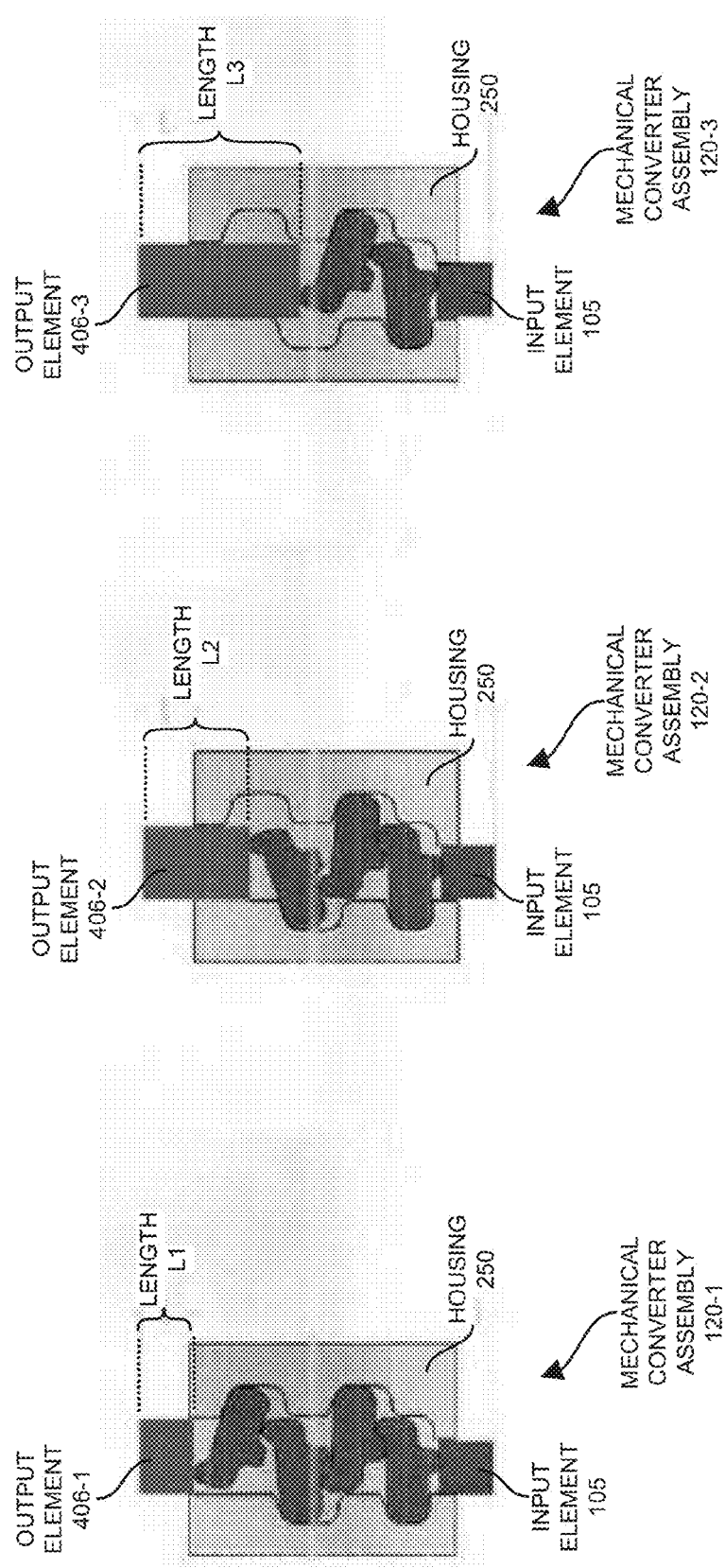
FIG. 4 is an example side-view diagram illustrating fabrication of different mechanical converter assemblies using a different number of levers according to embodiments herein.

FIG. 4 is an example diagram illustrating fabrication of mechanical converter assemblies using a different number of levers according to embodiments herein.

As shown, the housing 250 associated with mechanical converter assembly 120 can accommodate any suitable number of levers. For example, mechanical converter assembly 120-1 includes 4 levers; mechanical converter assembly 120-2 includes three levers; and mechanical converter assembly 120-3 includes two levers.

As would be expected, the mechanical converter assembly 120 provides different amounts of gains depending upon the number of levers that reside in respective housing 250. For example, the mechanical converter assembly 120-1 provides a higher amount of translational gain than mechanical converter assembly 120-2; the mechanical converter assembly 120-2 provides a higher amount of translational gain than mechanical converter assembly 120-3. Thus, in these example embodiments, the mechanical converter assembly 120-3 would provide the least amount of translational gain; mechanical converter assembly 120-1 would provide the most amount of translational gain.

As further shown, a respective length of the output element 406 of each mechanical converter assemblies 120-1, 120-2, 120-3, can be modified such that a single housing 250 can be used for a number of different lever applications. For example, mechanical converter assembly 120-1 includes four levers. In this instance, as shown, the length of output element 406-1 is length, L1.

Mechanical converter assembly 120-2 includes three levers. In this instance, because the mechanical converter assembly 120-2 includes one less lever than mechanical converter assembly 120-1, the output element 406-2 of mechanical converter assembly 120-2 is of length, L2.

Mechanical converter assembly 120-3 includes two levers. In this instance, because the mechanical converter assembly 120-2 includes two less levers than mechanical converter assembly 120-1, the output element 406-3 of mechanical converter assembly 120-3 is of length, L3.

Thus, because of the different length of output elements 406 to account for different numbers of installed levers, the mechanical converter assemblies 120 are swappable to provide different amounts of translational gain in a respective application.

As previously discussed, fabrication of one or more of the levers 210 in lever stack 122 to be flexible, bendable, etc., (via thinning or fabricating with flexible material) is useful. For example, in such an instance, translation of a received mechanical drive force (such as from driver resource 145 or a backlash from element 125) through the lever stack 122 at least partially deforms one or more of the multiple levers 210 from their respective original shapes. Subsequent to dissipation of the translated mechanical drive force through the lever stack 122, the one or more of the multiple levers 210 revert back to their respective original shapes. Thus, the lever stack 122 of multiple levers 210 between the input element 105 and the output element 106 can be configured to compress during translation of a force through the lever stack 122 due to flexing of one or more of the multiple levers 210 in the lever stack 122. The one or more deformed multiple levers 210 revert back to their original shapes upon dissipation of the translated force.

Thus, the lever stack 122 and corresponding levers 210 disposed between a respective input elements 105 and output element 106 can be configured to provide spring-like qualities. As previously discussed, these spring-like qualities may alleviate the need for inclusion of spring resource 199 disposed between the output element 106 and the element 125. However, an alternative bias device may be added to provide a return force which may substitute for that provided by the spring.

Figure 5:
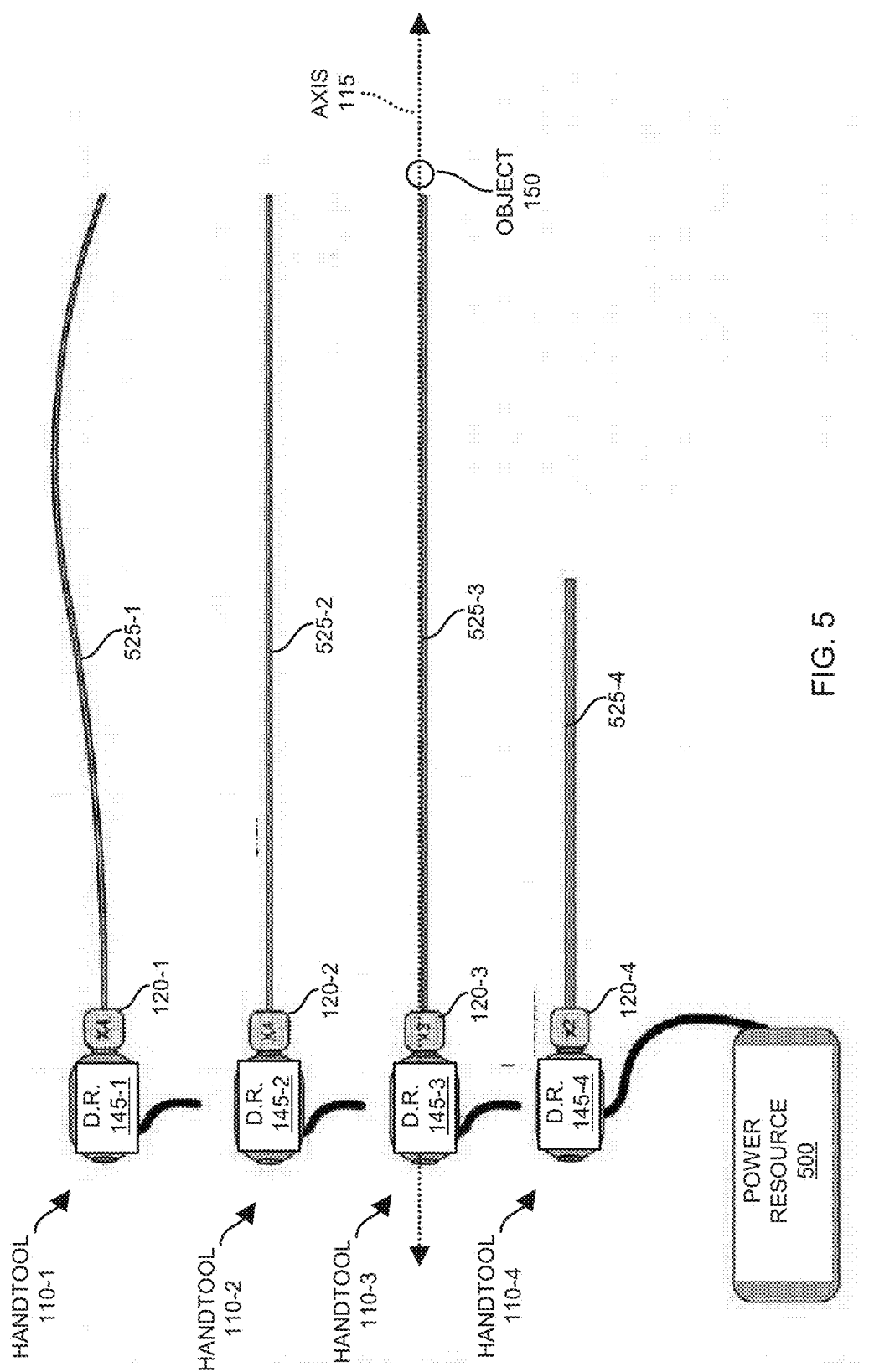
FIG. 5 is an example side-view diagram illustrating multiple hand tools including a respective mechanical converter assembly according to embodiments herein.

FIG. 5 is an example diagram illustrating multiple hand tools according to embodiments herein.

Embodiments herein can include fabricating a respective hand tool 110 via any suitable combination of a driver resource, mechanical converter assembly (such as a mechanical multiplier), and corresponding drive element (such as a shaft). As previously discussed, the mechanical gain (to obtain a particular back-and-forth stroke length) and shape of shafts associated with each hand tool can be tailored for different applications.

More specifically, in this example embodiment, hand tool 110-1 comprises driver resource 145-1, mechanical converter assembly 120-1 (such as 4 levers), and flexible lithotripsy shaft 525-1.

Hand tool 110-2 comprises driver resource 145-2, mechanical converter assembly 120-1 (such as 4 levers), and rigid or semi-rigid lithotripsy shaft 525-2.

Hand tool 110-3 comprises driver resource 145-3, mechanical converter assembly 120-2 (such as 3 levers), and lithotripsy shaft 525-3.

Hand tool 110-4 comprises driver resource 145-4, mechanical converter assembly 120-3 (such as 2 levers), and lithotripsy shaft 525-4.

Note that further embodiments herein include a resource such as power system 500. As its name suggests, power resource 500 provides the energy (such as one or more electrical signals, one or more pneumatic signals, etc.) to activate respective driver resources in accordance with control input provided by a hand tool operator.

Figure 6:
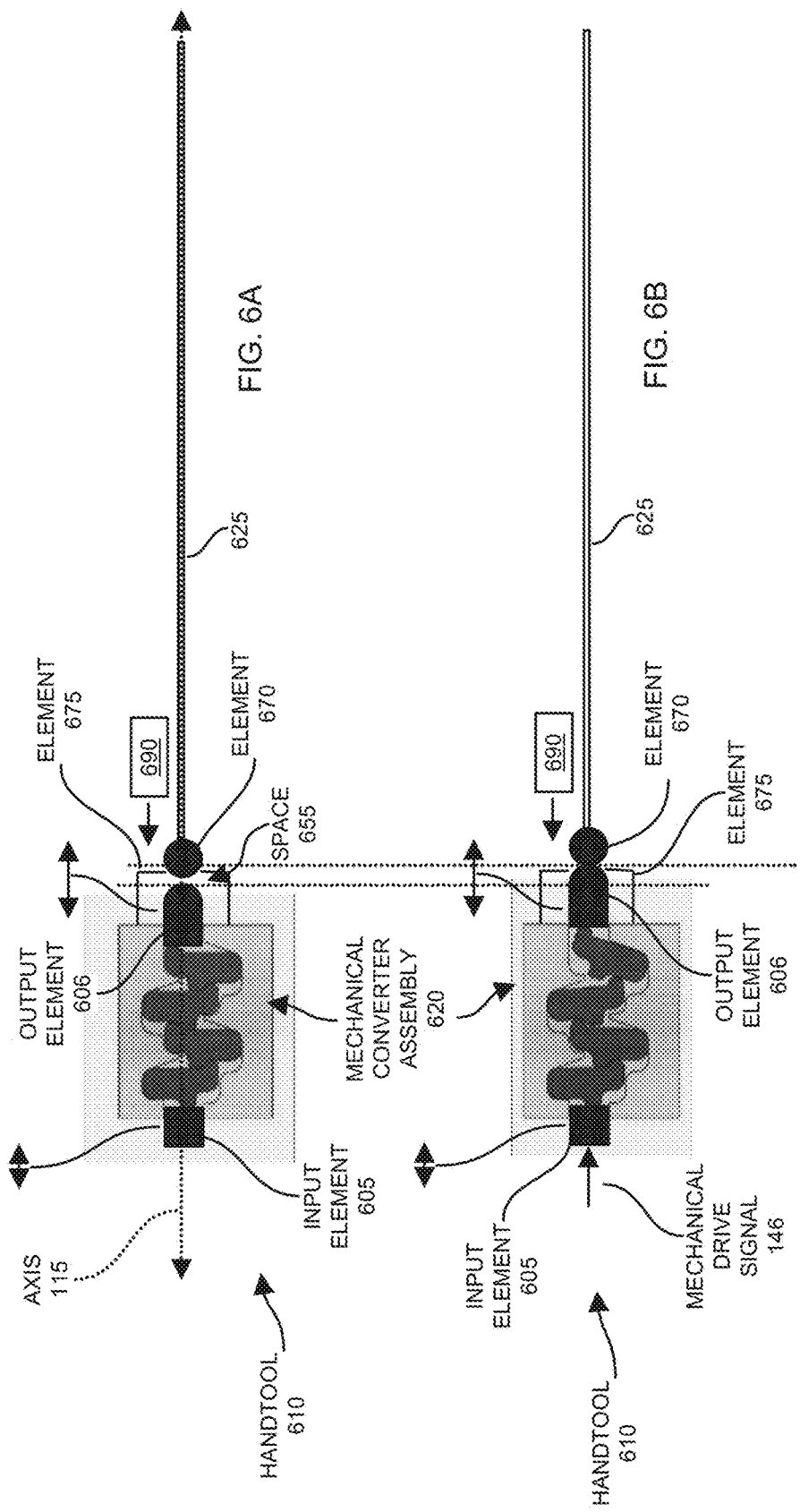
FIGS. 6A and 6B are example side-view diagrams illustrating different states of a hand tool according to embodiments herein.

FIGS. 6A and 6B are example side-view diagrams illustrating a hand tool according to embodiments herein.

In particular, FIG. 6A is an example side-view diagram illustrating a mechanical converter assembly 620 and corresponding drive element 625 resting in an initial condition in which substantially little or no force is applied to the input element 605. During such initial conditions, note that there is a space 655 between the output element 606 of mechanical converter assembly 620 and element 670 (such as a mass of metal, hard plastic, etc.) disposed at the proximal end of shaft 625. Element 670 can be affixed to proximal end of element 625.

Further, note that hand tool 610 can include spring 690 that applies a force to the shaft 625 and/or corresponding element 670 towards element 675 of mechanical converter assembly 620. This ensures that the element 670 is in a position to be struck by output element 606 upon application of force to input element 605.

In a manner as previously discussed, application of mechanical drive signal 646 to input transfer element 605 as shown in FIG. 6B causes the respective levers in mechanical converter assembly 620 to advance the output element 606 through space 655. As previously discussed, the mechanical converter assembly 620 provides translational gain along a respective axis. Eventually, based on application of a force to input element 605, the output element 606 moves and strikes the element 670, causing the shaft 625 (and element 670) of hand tool 610 to move along axis 115 away from mechanical converter assembly 620. Movement of the output element 606 through the space 655 ensures that a sufficient amount of gathered momentum is transferred from input element 605 and corresponding levers to the element 670 and shaft 625, causing a combination of the element 670 and shaft 625 to move to the right as shown in FIG. 6B (with respect to FIG. 6A).

The termination of applying the force to input transfer element 605 causes the components (such as input transfer element 605, levers in mechanical converter assembly 620, output transfer element 606, element 670, and shaft 625) to move back into the initial position as shown in FIG. 6A. As previously discussed, a spring such as spring resource 199 can be used to assist in returning the output element 606 and corresponding levers in mechanical converter assembly 620 back to their starting positions as shown in FIG. 6A after the force applied to input element 605 is terminated.

Repeated application and termination of the mechanical drive signal 646 causes the output element 606 to reciprocate along axis 115. In such an instance, as the output element 606 repeatedly strikes the element 670, the shaft 625 (driven element) and element 670 reciprocate as well along axis 115.

Figure 7:
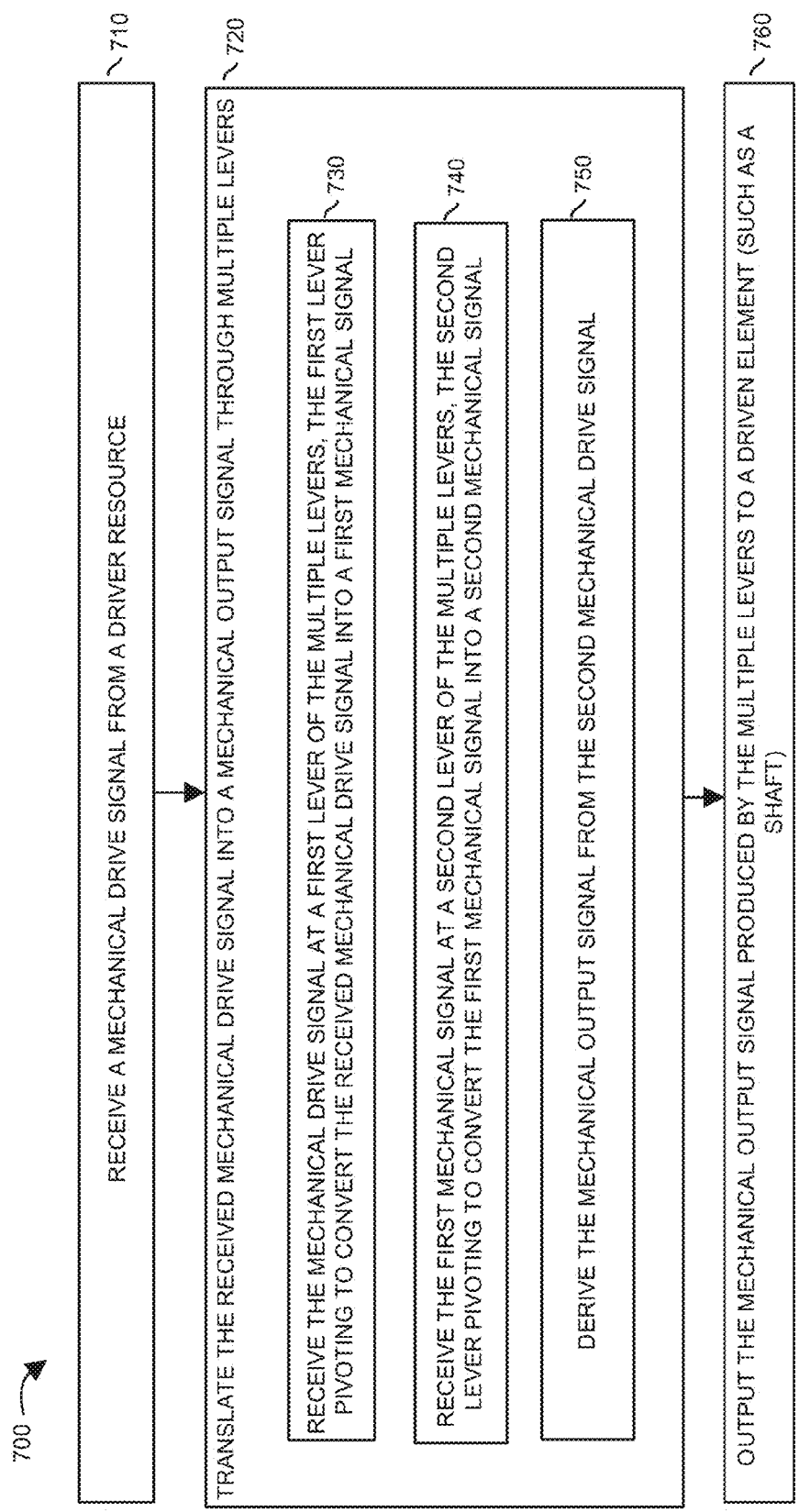
FIG. 7 is an example diagram illustrating of a method according to embodiments herein.

FIG. 7 is a flowchart 700 illustrating an example method according to embodiments. Note that there will be some overlap with respect to concepts as discussed above.

In processing block 710, the mechanical converter assembly 120 receives a mechanical drive signal 146 from a driver resource 145.

In processing block 720, the mechanical converter assembly 120 translates the received mechanical drive signal 146 into a mechanical output signal through multiple levers.

Execution of processing block 720 can include execution of subprocessing blocks 730, 740, and 750. In processing block 730, the mechanical converter assembly 120 receives the mechanical drive signal 146 at a first lever of the multiple levers, the first lever pivots to convert the received mechanical drive signal 146 into a first mechanical signal. In processing block 740, the mechanical converter assembly 120 receives the first mechanical signal at a second lever of the multiple levers. The second lever pivots to convert the first mechanical signal into a second mechanical signal. In processing block 750, the mechanical converter assembly 120 derives the mechanical output signal (as outputted from the mechanical converter assembly 120) from the second mechanical drive signal.

In processing block 760, the mechanical converter assembly 120 output the mechanical output signal produced by the multiple levers to a driven element 125 (such as a shaft).

Figure 8:
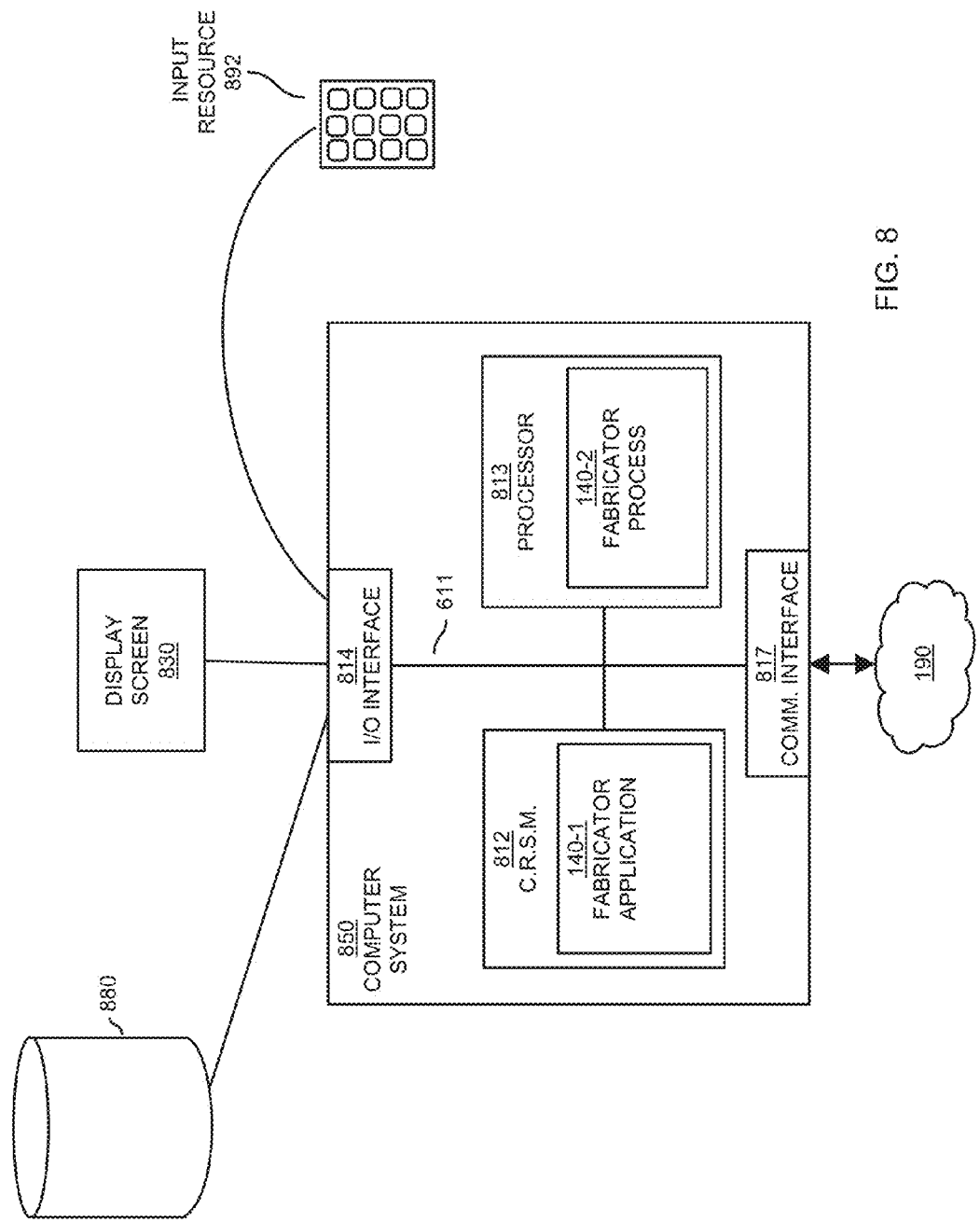
FIG. 8 is an example diagram illustrating a computer system (such as a fabricator resource) executing one or more instructions to create a mechanical converter assembly and/or hand tool according to embodiments herein.

FIG. 8 is an example diagram illustrating a computer system (such as disposed in a fabricator resource) executing one or more instructions to produce a mechanical converter assembly according to embodiments herein. Any of the different processing techniques to fabricate a mechanical converter assembly having desired characteristics can be achieved via execution of software code on computer processor hardware.

As shown, computer system 850 (e.g., computer processor hardware) of the present example can include an interconnect 811 that couples computer readable storage media 812 such as a non-transitory type of media (i.e., any type of hardware storage medium) in which digital information can be stored and retrieved. The computer system 850 can further include processor 813 (i.e., computer processor hardware such as one or more processor co-located or disparately located processor devices), I/O interface 814, communications interface 817, etc.

Computer processor hardware (i.e., processor 813) can be located in a single location or can represent multiple resources distributed amongst multiple locations in a fabrication environment.

As its name suggests, I/O interface 814 provides connectivity to resources such as repository 880, control devices (such as input resource 892), one or more display screens, etc.

Computer readable storage medium 812 can be any hardware storage device to store data such as memory, optical storage, hard drive, floppy disk, etc. In one embodiment, the computer readable storage medium 812 stores instructions and/or data.

Communications interface 817 enables the computer system 850 and processor resource 813 to communicate over a resource such as a network 190. I/O interface 814 enables processor resource 813 to access data from a local or remote location, control a respective display screen, receive input, etc.

As shown, computer readable storage media 812 can be encoded with fabricator application 140-1 (e.g., software, firmware, etc.) executed by processor 813 (computer processor hardware). Fabricator application 140-1 can be configured to include instructions to implement any of the processing operations as discussed herein.

During operation of one embodiment, processor 813 accesses computer readable storage media 812 via the use of interconnect 811 in order to launch, run, execute, interpret or otherwise perform the instructions in fabricator application 140-1 stored on computer readable storage medium 812.

Execution of the fabricator application 140-1 produces processing functionality such as fabricator process 140-2 in processor resource 813. In other words, the fabricator process 140-2 associated with processor resource 813 represents one or more aspects of executing fabricator application 140-1 within or upon the processor resource 813 in the computer system 850.

Those skilled in the art will understand that the computer system 850 can include other processes and/or software and hardware components, such as an operating system that controls allocation and use of hardware resources to execute fabricator application 140-1.

In accordance with different embodiments, note that computer system can be any suitable type of computer device. The computer system 850 may reside at any location or multiple locations in a fabrication environment. As mentioned, the computer system 850 can be included in any suitable resource such as in one or more fabricator resources to implement any functionality as discussed herein.

Figure 9:
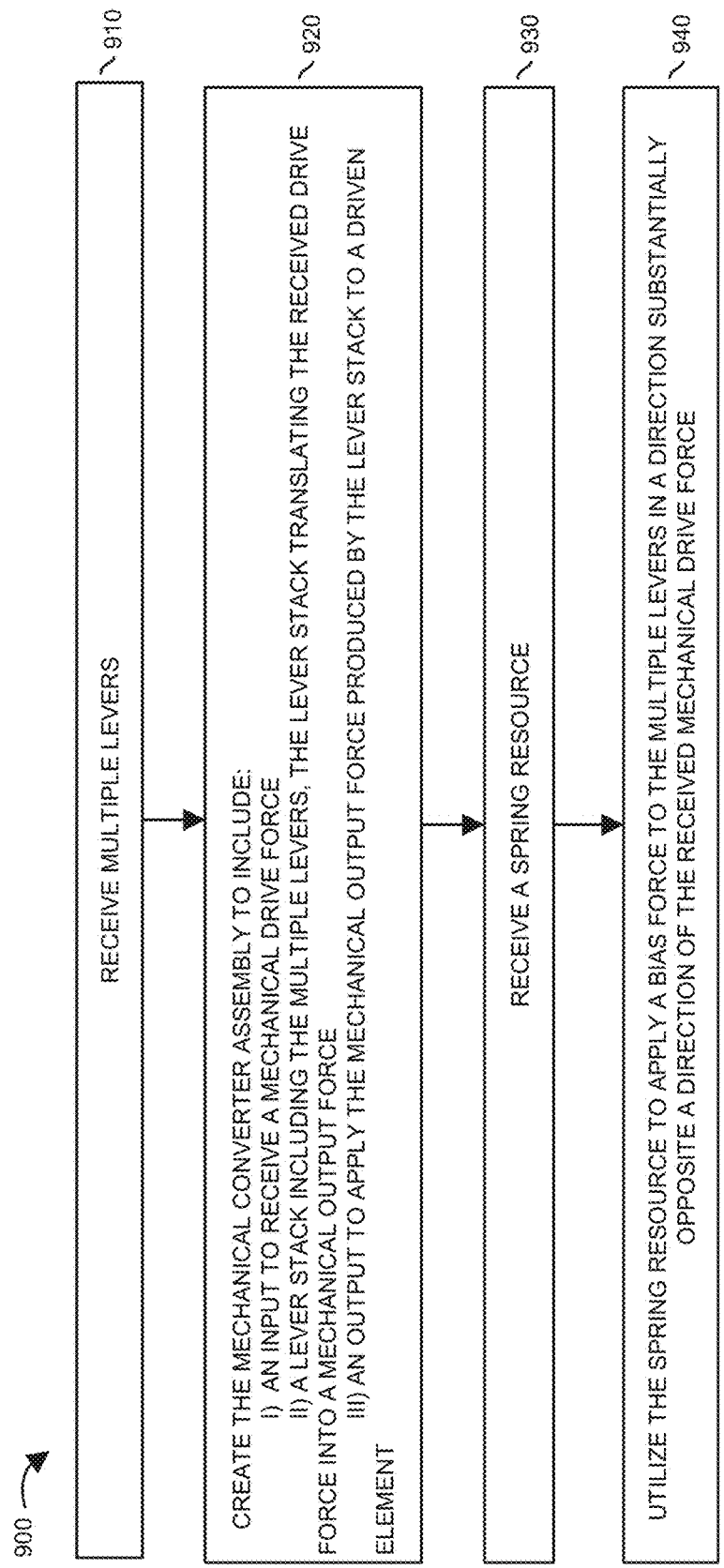
FIG. 9 is an example diagram illustrating a method of fabricating a mechanical converter assembly and/or hand tool according to embodiments herein.

FIG. 9 is a flowchart 900 illustrating an example method of fabricating an assembly according to embodiments. Note that there will be some overlap with respect to concepts as discussed above.

In processing block 910, a fabricator resource (via fabricator application 140-1 and/or fabricator process 140-2) receives multiple levers (such as levers 210-1, 210-2, 210-3, and 210-4).

In processing block 920, the fabricator resource creates the mechanical converter assembly 120 to include: i) an input element 105 to receive a mechanical drive force, ii) a lever stack 122 including the multiple levers, the lever stack 122 translating the received drive force into a mechanical output force, and iii) an output element 106 to apply the mechanical output force produced by the lever stack 122 to a driven element 125.

In processing block 930, the fabricator resource receives a spring resource.

In processing block 940, the fabricator resource utilizes the spring resource 199 to apply a bias force to the multiple levers in the lever stack 122 in a direction substantially opposite a direction of the received mechanical drive force.

In accordance with further embodiments, the fabricator resource can be configured to produce the mechanical converter assembly to include a housing 250 in which the multiple levers 210 reside. As mentioned, the multiple levers can include at least a first lever 210-1, second lever 210-2, etc. The first lever 210-1 can be configured to receive the mechanical drive force from the input element 105. The first lever 210-1 pivots in the housing 250 to convert the received mechanical drive force into a second drive force conveyed up the lever stack 122 to the second lever 210-2. The second lever 210-2 pivots to convert the second mechanical drive force up the stack 122 toward the output, and so on.

FIG. 10 is an example perspective-view diagram illustrating a mechanical converter assembly according to embodiments herein.

As shown in this example, the mechanical converter assembly 1020 includes multiple levers and generally operates in a similar manner as previously discussed with respect to other embodiments. However, in this example embodiment, as further shown, the application of the mechanical drive signal 146 along axis 115 (a first direction) to the input of mechanical converter assembly 1020 causes a tip of the right-most lever in the mechanical converter assembly 1020 to move in a direction from the START position to the MOVED position along axis 1015. Thus, the output force or output motion from the mechanical converter assembly 1020 is in a different direction than the input direction of mechanical motion (mechanical drive signal 146).

In accordance with further embodiments, the axis 1015 is substantially orthogonal with respect to axis 115, although the mechanical converter assembly 1020 can be configured to provide an output force in any suitable direction with respect to axis 115.

FIG. 11 is an example side-view diagram illustrating a mechanical converter assembly according to embodiments herein.

As shown in this example, the mechanical converter assembly 1120 includes multiple levers and generally operates in a similar manner as previously discussed with respect to other embodiments. However, in this example embodiment, as further shown, the application of the mechanical drive signal 146 along axis 115 (a first direction) to the input of mechanical converter assembly 1120 causes a tip of the right-most lever in the mechanical converter assembly 1120 to move in a direction from the START position to the MOVED position along axis 1015. Thus, the output force or output motion from the mechanical converter assembly 1120 is in a different direction than the input direction of mechanical motion (mechanical drive signal 146).

In accordance with further embodiments, the axis 1015 is substantially orthogonal with respect to axis 115, although the mechanical converter assembly 1120 can be configured to provide an output force in any suitable direction with respect to axis 115.

Note again that techniques herein are well suited for providing translational gain in a hand tool via multiple levers. However, it should be noted that embodiments herein are not limited to use in such applications and that the techniques discussed herein are well suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

I claim:

1. A lithotripsy system comprising:
  a shaft; and
  a mechanical converter assembly, the mechanical converter assembly comprising:
    an input element to receive a mechanical drive signal from a driver resource;
    a lever stack including multiple levers, the lever stack translating the mechanical drive signal received at the input element into a mechanical output signal that translationally moves a shaft, the mechanical drive signal is a mechanical drive force and the mechanical output signal is a mechanical output force;
    an output element operable to apply the mechanical output signal produced by the lever stack to the shaft, the lever stack further includes: a housing in which the multiple levers are disposed, the multiple levers including at least a first lever and a second lever, the first lever receiving the mechanical drive force from the input element, the first lever pivoting in the housing to convert the mechanical drive force into a first internal drive force conveyed up the lever stack to the second lever, the second lever pivoting to convert the first internal drive force up the lever stack toward the output element;
    a spring disposed between the shaft and the output element and configured to assist in returning the output element to an initial condition and to apply a force to the shaft towards the output element, wherein the initial condition is when little force or no force is applied to the input element.

2. The lithotripsy system as in claim 1 wherein, the spring resource applies a bias force to the multiple levers in a direction opposite the received mechanical drive force.

3. The lithotripsy system as in claim 2, wherein a magnitude of the received mechanical drive signal varies over time, variations in the magnitude of the mechanical drive signal causing the output element to repeatedly strike the shaft.

4. The lithotripsy system as in claim 1, wherein the-shaft includes a proximal end and a distal end, the output element reciprocates along a translational axis through the lever stack at times the mechanical drive signal is applied to the input element, the output element repeatedly striking the proximal end of the shaft causing the shaft to reciprocate at times the mechanical drive signal is applied to the input element.

5. The lithotripsy system as in claim 1, wherein the lever stack further includes a first pin and a second pin, the first lever pivoting about the first pin, and the second lever pivoting about the second pin.

6. The lithotripsy system as in claim 1, wherein the lever stack further includes: a first lever and a second lever; a housing in which the first lever and second lever are disposed, the housing including a first surface and a second surface; and the first lever pivoting with respect to the first surface, and the second lever pivoting with respect to the second surface.

7. The lithotripsy system as in claim 1, wherein the lever stack provides translational gain in which an amount of translational movement of the input element results in a greater amount of corresponding translational movement of the output element.

8. The lithotripsy system as in claim 1, wherein each of the multiple levers is fabricated from an elastic material and at least one of the multiple levers is deformed from its original shape at times the mechanical drive force is applied to the lever stack and reverts back to its original shape at times subsequent to dissipation of the mechanical drive force.

9. The lithotripsy system as in claim 1, wherein the lever stack of multiple levers is disposed between the input element and the output element, the lever stack of multiple levers compresses at times of translation of the mechanical drive force according to flexing of at least one of the multiple levers, and the flexed of at least one of the multiple levers reverts back to its original shape at times subsequent to dissipation of the mechanical drive force.

10. The lithotripsy system as in claim 1, wherein the lever stack provides translational motion gain between the input element and the output element.

11. The lithotripsy system as in claim 1, wherein at times the mechanical drive signal is applied to the input element, the lever stack translates the mechanical drive signal into a mechanical output signal that translationally moves the output element to advance through a space between the shaft and the output element and strike the shaft.

* * * * *